United States Patent
Coville

(10) Patent No.: US 7,294,311 B2
(45) Date of Patent: Nov. 13, 2007

(54) CLOT RETAINER

(75) Inventor: William E. Coville, Levittown, PA (US)

(73) Assignee: Bio/Data Corporation, Horsham, PA (US)

( * ) Notice: Subject to any disclaimer, the term of this patent is extended or adjusted under 35 U.S.C. 154(b) by 0 days.

(21) Appl. No.: 11/099,350

(22) Filed: Apr. 5, 2005

(65) Prior Publication Data

US 2005/0226785 A1    Oct. 13, 2005

Related U.S. Application Data

(60) Provisional application No. 60/559,508, filed on Apr. 5, 2004.

(51) Int. Cl.
*B01L 11/00* (2006.01)
*G01N 1/18* (2006.01)

(52) U.S. Cl. .................. 422/101; 422/73; 422/99; 422/102; 436/63; 436/69; 436/177; 210/645; 210/780

(58) Field of Classification Search ............. 436/69, 436/63, 174, 177; 422/73, 99, 101, 102, 422/103; 73/64.41; 600/368, 369; 210/516, 210/518, 645, 780, 781, 782
See application file for complete search history.

(56) References Cited

U.S. PATENT DOCUMENTS

| | | | | |
|---|---|---|---|---|
| 3,782,548 | A | * | 1/1974 | Bowen .................... 210/94 |
| 3,837,376 | A | * | 9/1974 | Brown et al. ............. 141/1 |
| 3,879,295 | A | * | 4/1975 | Glover et al. ............ 210/516 |
| 3,970,565 | A | * | 7/1976 | Ahlstrand et al. ........ 210/359 |
| 5,980,734 | A | * | 11/1999 | Itoh ........................ 210/85 |
| 6,398,956 | B1 | * | 6/2002 | Coville et al. ......... 310/321.75 |

FOREIGN PATENT DOCUMENTS

| | | | |
|---|---|---|---|
| JP | 11-083847 | | 3/1999 |
| JP | 11-83847 | * | 3/1999 |
| JP | 2003-043032 | | 2/2003 |
| JP | 2003-43032 | * | 2/2003 |

* cited by examiner

*Primary Examiner*—Maureen M. Wallenhorst
(74) *Attorney, Agent, or Firm*—Volpe & Koenig PC

(57) ABSTRACT

A clot retainer for generally separating liquid from solid components in a specimen enclosed in a container having a closure. The clot retainer includes fingers that are adapted to displace solid components of the specimen. The clot retainer can be inserted through the closure of the container without removing the container. A method of separating liquid from solid components in a specimen is also disclosed.

35 Claims, 6 Drawing Sheets

CLOT RETAINER

CROSS REFERENCE TO RELATED APPLICATION

This application claims priority to and benefit of U.S. Provisional Patent Application 60/559,508, filed Apr. 5, 2004, which is hereby incorporated by reference in its entirety as if fully set forth herein.

BACKGROUND

The present invention relates generally to medical diagnostic methods and devices. More particularly, the present invention relates to a more effective and controlled method of processing a patient blood specimen using a disposable device to displace or dislodge a blood clot in a collection tube to assist in separating the serum from the rest of the blood specimen.

The processing of a patient blood specimen to obtain serum has been a problem for clinical laboratories and specifically for analytical instrument manufacturers supplying products to those laboratories. The need to separate the fibrin clot and cellular matter from the serum, and keeping them separated from each other, remains a continuous and unresolved challenge. In current practice, the closed specimen collection container must be de-capped, manually rimmed ("rimming the clot" to separate the fibrin clot from the container wall using an applicator stick), and then recapped, prior to centrifugation of the specimen container. These processes result in physical, chemical, and biological changes that affect the quality of the serum or otherwise limit its usefulness or condition. Without consistent effective and controlled preparation, analytical quality serum may not be obtained.

The condition of the clotted specimen is dependent on a number of factors including patient condition, additives in the collection tube, the collection technique and the length of time the specimen is allowed to clot, temperature, transport condition etc. Various additives have been used to increase the speed of clot formation and the quality of extracted serum. The clotted specimen may be a loose floating gelatinous mass, mixture of cells, fibrin strands and serum, or a firm clot with the serum trapped below the fibrous surface. To ensure the specimen is not attached to the walls of the container and trapping serum, the specimen tube must be opened and the clot dislodged by mechanical stirring or scraping, called rimming, prior to centrifugation. Opening the tube presents a biohazardous risk to the technician, challenges the integrity of the specimen, and may cause other artifactual changes to the specimen.

A number of methods have been developed to physically separate the constituents. The methods range from the insertion of glass or plastic barriers, to chemical additives to enhance clot formation, or coatings to prevent hemolysis, to the incorporation of gel materials in the collection tube to separate the serum and clot. The specific gravity of the gels is such that after centrifugation, the gel is positioned between the cellular and liquid layers. The use of gels or additives results in the introduction of unwanted, unrelated materials into automated sample transfer systems, and physically occludes the fluidic transfer systems and interferes with further analyses. Present standards require that laboratories verify that these gels do not affect the analysis performed. The ideal preparation method would not require the opening of the specimen tube or the introduction of any foreign material into the specimen.

When a specimen is received for analysis, the sample to be derived from the specimen is identified by the analysis requested. If a serum sample is required, the traditional method of preparation typically requires "rimming the clot" followed by centrifugation. After rimming, the specimen is centrifuged to cause the clot to settle to the bottom of the tube and leaving the serum as the top layer. However, both of these steps can have adverse effects. The rimming process can potentially expose the technician to biohazardous material, and creates biohazardous waste that must be handled and discarded. Additionally, the sample may become contaminated and physical damage caused by this process can result in creating interferents that may affect the analysis. The centrifugation process may also damage the specimen or cause changes in the sample.

There is a need in the art for a more safe effective and controlled method of processing a patient blood specimen. It would be advantageous to provide a clot retainer that can harvest serum from a patient blood collection tube or container without the removal of the septum, cap or stopper. It would also be advantageous to provide a clot retainer that permits the collection or retrieval of serum from the sealed container or collection tube regardless of the condition or physical characteristics of the clotted blood in the container.

SUMMARY

One embodiment of the present invention is directed to a clot retainer for generally separating serum from a patient blood specimen enclosed in a container having a closure. The clot retainer includes an elongate shaft. A piercing tip is positioned on an end of the elongate shaft and is adapted to pierce the closure on the container to insert the clot retainer into the container without removal of the closure. Fingers are positioned on the elongate shaft and are adapted to displace solid components of the patient blood specimen toward a base of the container while allowing the serum to flow through interstices between the fingers. Each of the fingers is moveable from a first position, in which the finger is ready for use and is in a generally radially extending position, to a second position, in which the finger is ready for insertion and is in a generally axially extending position along the elongate shaft. Each of the fingers is in the second position during insertion prior to returning to the first position after insertion.

In a separate aspect, the present invention is directed to a clot retainer for generally separating liquid from solid in a specimen enclosed in a container having a closure. The clot retainer includes an elongate shaft. A piercing tip is positioned on an end of the elongate shaft and is adapted to pierce the closure on the container to insert the clot retainer into the container without removal of the closure. Fingers are positioned on the elongate shaft and are adapted to displace solid components of the specimen toward a base of the container while allowing the liquid to flow through interstices between the fingers. Each of the fingers is moveable from a first position, in which the finger is ready for use and is in a generally radially extending position, to a second position, in which the finger is ready for insertion and is in a generally axially extending position along the elongate shaft. Each of the fingers is in the second position during insertion prior to returning to the first position after insertion.

In a separate aspect, the present invention is directed to a method of harvesting serum from a patient blood specimen. The method includes the steps of: providing a container enclosing a patient blood specimen, the container having a closure and a base; providing a clot retainer comprising an elongate shaft having a piercing tip positioned thereon and fingers mounted on the elongate shaft; inserting the clot retainer, piercing tip first, into the container by piercing the closure with the piercing tip; and displacing solid components from the patient blood specimen with the fingers toward the base of the container.

In a separate aspect, the present invention is directed to a combination closure and clot retainer for generally separating serum from a patient blood specimen enclosed in a container. The combination includes an elongated shaft including a base member having first and second ends. A piercing member is slidably disposed on the first end of the base member. A closure is positioned on the second end of the base member. A piercing tip is positioned on an end of the piercing member and adapted to pierce a clot in the specimen. Fingers are positioned on the elongate shaft and are adapted to displace solid components of the patient blood specimen toward a base of the container while allowing the serum to flow through interstices between the fingers.

In a separate aspect, the present invention is directed to a combination closure and clot retainer for generally separating serum from a patient blood specimen enclosed in a container. The combination includes a closure adapted to engage the container and having a passageway therethrough to allow fluid transfer therethrough. A coil defining at least one coil winding is positioned on a side of the closure that faces a base of the container when the closure is engaged with the container. The at least one coil winding is adapted to displace solid components of the patient blood specimen toward the base of the container while allowing the serum to flow past the at least one coil winding.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 6 is a perspective view of the clot retainer of FIG. 1 with a replacement closure attached thereto; the replacement closure includes a luer lock connector or the like.

DETAILED DESCRIPTION OF THE PREFERRED EMBODIMENT(S)

Figure 1A:
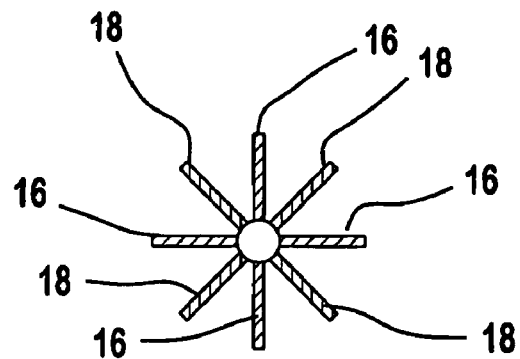
FIG. 1A is an overhead view of a set of fingers of the clot retainer of FIG. 1.

Certain terminology is used in the following description for convenience only and is not limiting. The words "right," "left," "lower," and "upper" designate directions in the drawings to which reference is made. The words "inwardly" and "outwardly" refer to directions toward and away from, respectively, the geometric center of the clot retainer and designated parts thereof. The words "a" and "one", as used in the claims and in the corresponding portions of the specification, are defined as including one or more of the referenced item unless specifically stated otherwise. The terminology includes the words noted above as well as derivatives thereof and words of similar import.

Figure 1:
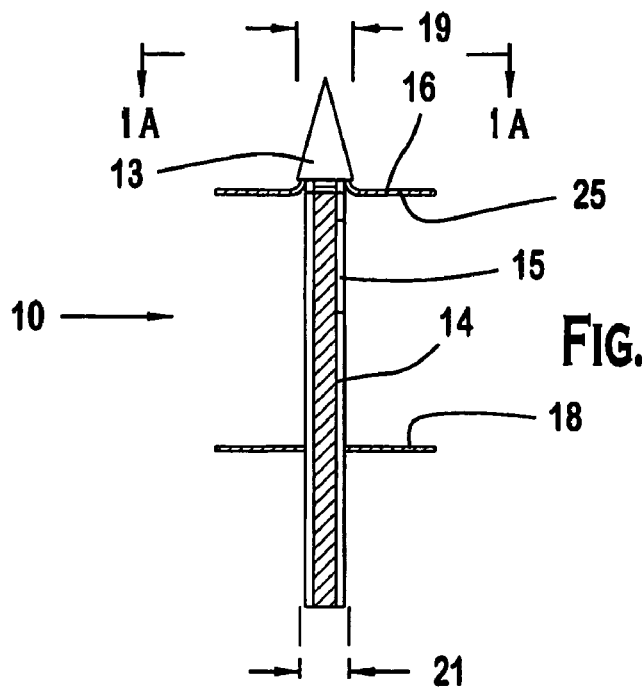
FIG. 1 is a side view of the clot retainer of the present invention.

Referring now to FIGS. 1-3C, a preferred embodiment of a clot retainer 10 for separating liquid from solid in a specimen in accordance with the present invention is shown. The clot retainer 10 is preferably used to separate serum 34 from a patient blood sample 26. As best shown in FIG. 1, the clot retainer 10 includes a piercing tip 12, an elongate shaft 14, and fingers 16, 18 preferably grouped into first and second sets of collapsible fingers 16, 18, respectively. Referring to FIGS. 3A and 3B, the piercing tip 12 is adapted to pierce a septum cap, stopper, or closure 20 of a collection tube or container 22 and a clot 24 of a specimen 26 to be processed.

The length of the shaft 14 may vary depending on the size of the collection tube 22. The shaft 14 may also be of such a length that extends through the septum 20, and/or may be hollow or segmented to allow the test sample 26 to flow through the shaft 14. The shaft 14 may include at least one recess 15 configured to receive at least one of the fingers 16, 18 therein during insertion of the clot retainer 10 through the closure 20.

Referring to FIGS. 1 and 3A-3C, the piercing tip 12 is positioned on an end of the shaft 14 and is adapted to pierce the closure 20 on the container 22 to insert the clot retainer 10 into the container 22 without removal of the closure 20. The piercing tip 12 is preferably generally conically shaped and has a base 13, located proximate to the shaft 14, having a base diameter 19 greater than a shaft diameter 21 of the elongate shaft 14. It is preferable that the general overall diameter of the shaft 14 and the fingers 16, 18, when the fingers 16, 18 are in a second position (described in detail below), is generally the same as or less than the base diameter 19 of the piercing tip 12.

The clot retainer 10 preferably, but not necessarily, has two sets of fingers 16, 18 that extend radially outwardly from the shaft 14 in the first position. The fingers 16, 18 are positioned on the shaft 14 and are adapted to displace solid components, such as clot material 24 of the patient blood specimen, toward a base 23 of the container 22 while allowing serum 34 to flow through interstices between the fingers 16, 18. Each of the fingers 16, 18 is moveable from a first position (shown in FIG. 1), in which the fingers 16, 18 are ready for use and is in a generally radially extending position, to a second position (shown in FIG. 3A in which the second set of fingers 18 are vertically positioned), in which the fingers 18 are ready for insertion and are in a generally axially extending position along the elongate shaft 14. Each of the fingers 16, 18 is in the second position during insertion prior to returning to the first position after insertion. The clot retainer 10 may have only a single set of fingers 16, 18 or may have three or more sets of fingers 16, 18 and the fingers 16, 18 may have varying degrees of rigidity/flexibility appropriate to the nature of the specimen without departing from the scope of the present invention.

The first set of collapsible fingers 16 is preferably mounted on an upper part of the shaft 14 near the piercing tip 12, and the second set of collapsible fingers 18 is preferably positioned on the elongate shaft 14 and spaced apart from the first set of fingers 16. It is preferable that the first set of fingers 16 forms a layer 25 having a permeable free space of generally fifty (50%) percent or less. It is more preferable still that the layer 25 have a permeable free space of generally less than twenty-five (25%) percent. However, the permeable free space can be varied based on the particular application.

The second set of fingers 18 can be positioned on the lower part of the shaft 14 to remain above the clot 24 upon full insertion. Both sets of fingers 16, 18 may be mounted in subsets, for example four fingers per subset, or may be individually mounted to the shaft 14. The fingers 16, 18 are of such a length so as to enable them to contact a surrounding wall 28 of the collection tube 22. The first set of fingers 16 preferably squeeze the clot and disrupt it, while the second set of fingers 18 do the same and catch any floating clumps of fibrin strands.

Both sets of fingers 16, 18 preferably fold back along the shaft 14 when inserted through the septum 20 of the collection tube 22, preferably upon contacting the cap 20 due to the elastic property of the fingers 16, 18. The shaft 14 can include recesses along its sides for fingers 16, 18 to fold into during insertion. Once inside the collection tube 22, the fingers 16, 18 return to their original extended position, preferably through the elasticity of the fingers 16, 18, thereby disrupting and suspending the clot 24.

In the preferred embodiment, the shaft is made of a strong, non-reactive, non reactive material such as a polymer and the fingers 16, 18 are made of a durable, non-reactive, elastic material, such as a suitable polymer or elastomer. Fingers 16, 18 are preferably made of an elastic material that allows them to fold or collapse against the shaft 14 upon contact with the cap 20 and elastically spring back to a first radially extending position when not contacting the cap 20. The clot retainer 10 can be made from any suitable materials without departing from the present invention.

Figure 2A:
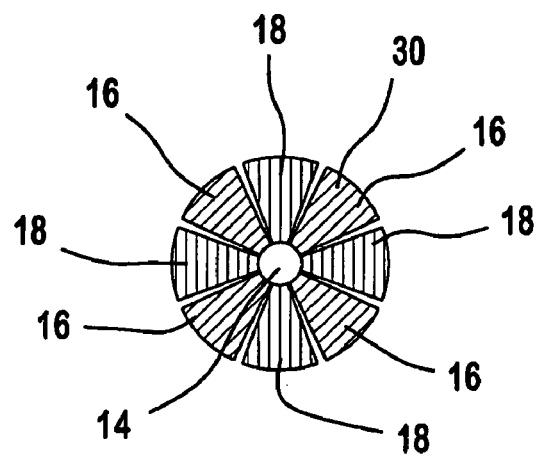
FIG. 2A is an overhead view of an increased width set of fingers of the clot retainer.
Figure 2B:
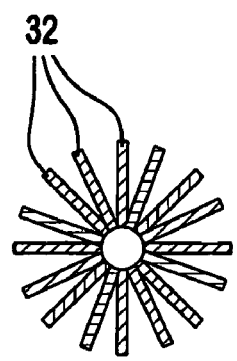
FIG. 2B is an overhead view of an increased quantity set of fingers of the clot retainer.

In addition, as shown in FIGS. 2A and 2B, the finger width 30, quantity 32, or position can be modified depending on the purpose of the application. FIG. 2A illustrates at least one of the fingers 16, 18 being wedge-shaped such that a finger width, as measured in a circumferential direction, of each wedge-shaped finger 16, 18 increases when moving along the finger 16, 18 in a generally radially outward direction.

FIG. 2B illustrates at least one of the fingers 16, 18 having a generally rectilinear shape such that the finger width, as measured in a direction tangential to a cross-section of the shaft 14 as taken perpendicular to a shaft longitudinal axis, is generally constant. However, one of ordinary skill in the art would recognize that the fingers 16, 18 and shaft 14 can be modified as necessary to make the clot retainer 10 more effective without deviating from the intent of the present invention.

Figure 3A:
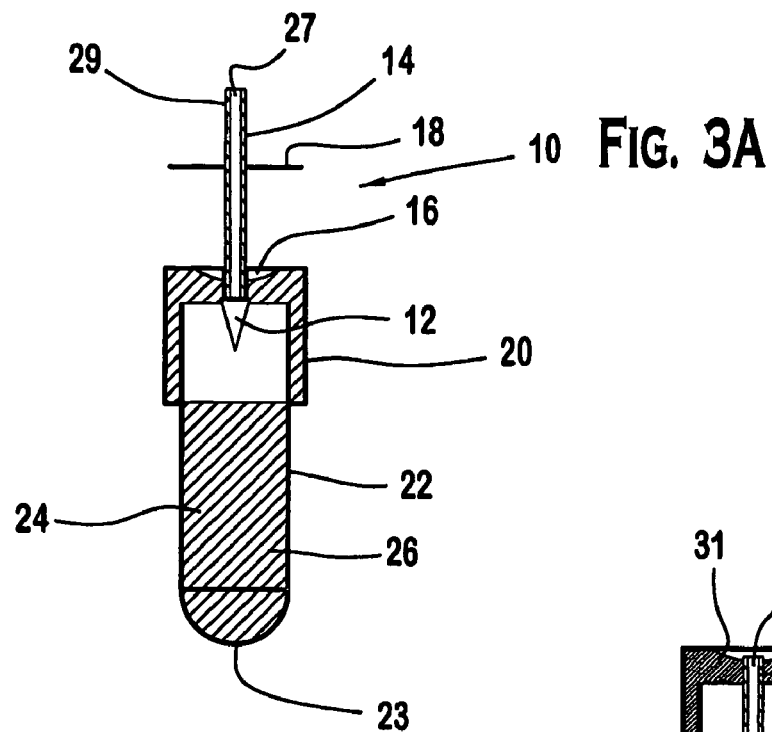
FIG. 3A is a side view of the clot retainer being used in conjunction with a collection tube and specimen at the initial insertion stage.
Figure 3B:
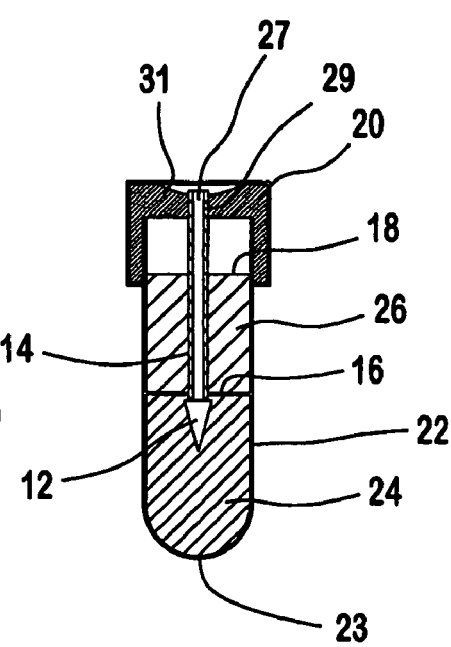
FIG. 3B is a side view of the clot retainer being used in conjunction with a collection tube and specimen at an intermediary insertion stage.

When allowing the test sample 26 to flow through the shaft 14 is desirable, the shaft 14 may include a passageway 27, shown in FIGS. 3A and 3B, that extends through at least a portion of the shaft 14. The passageway 27 is adapted to allow withdrawal of serum 34 from the container 22 while the shaft 14 is positioned through the closure 20.

Figure 3C:
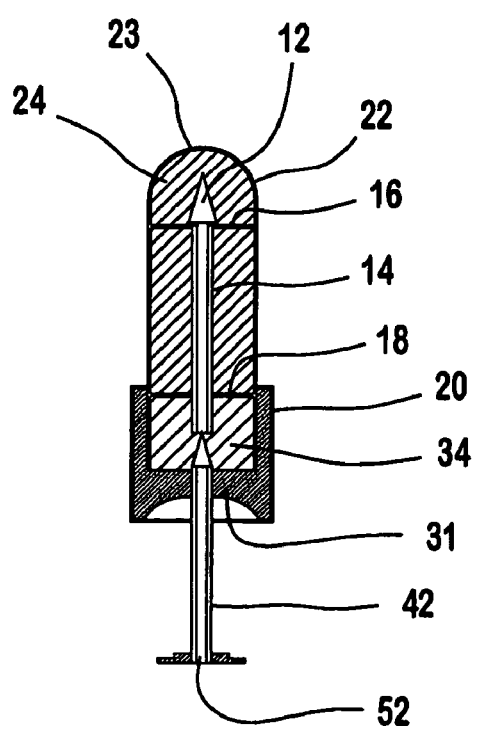
FIG. 3C is a side view of the clot retainer being used in conjunction with a collection tube and specimen at the full insertion stage.

FIGS. 3A-3C illustrate a preferred method of insertion of the clot retainer 10 of the present invention into a collection tube 22 containing a specimen 26. At the initial insertion stage, as illustrated by FIG. 3A, the piercing tip 12 is inserted through the septum 20 of the collection tube 22 positioned in a generally vertical direction with the septum 20 facing up. The first set of fingers 16 collapse during insertion through the septum 20.

Referring to FIG. 3B, at the intermediate stage of insertion, the piercing tip 12 pierces the clot 24, and when the first set of fingers 16 contact the clot 24, they disrupt any surface membranes that may be present and displace the clot 24 toward a base 23 of the collection tube 22 to induce the release of serum 34. The second set of fingers 18 fold in a similar manner as the first set of fingers 16 as they pass through the septum 20. Upon full insertion, the second set of fingers 18 remain above the clot 24.

Referring to FIG. 3C, the collection tube 22 is then inverted. The loose clot or any large segments thereof are supported on the upper and lower fingers 16, 18, and the serum 34 flows to the septum end 20 of the collection tube 22. The serum 34 can then be extracted, for example using a spike 42 as shown, and either filtered or centrifuged to remove the remaining cellular and solid components and, if desired, can be transferred directly to an analyzer.

Figure 4A:
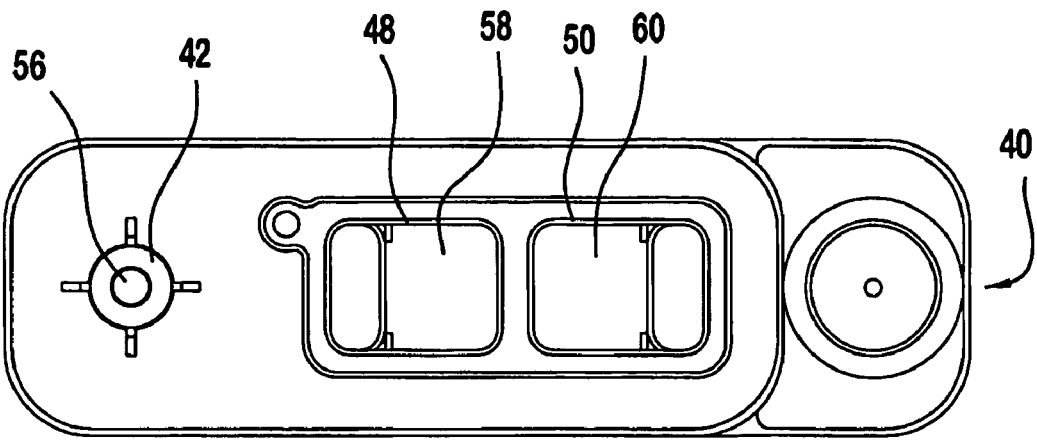
FIG. 4A is an overhead view of a filtration cell for use in conjunction with the clot retainer of the present invention.
Figure 4B:
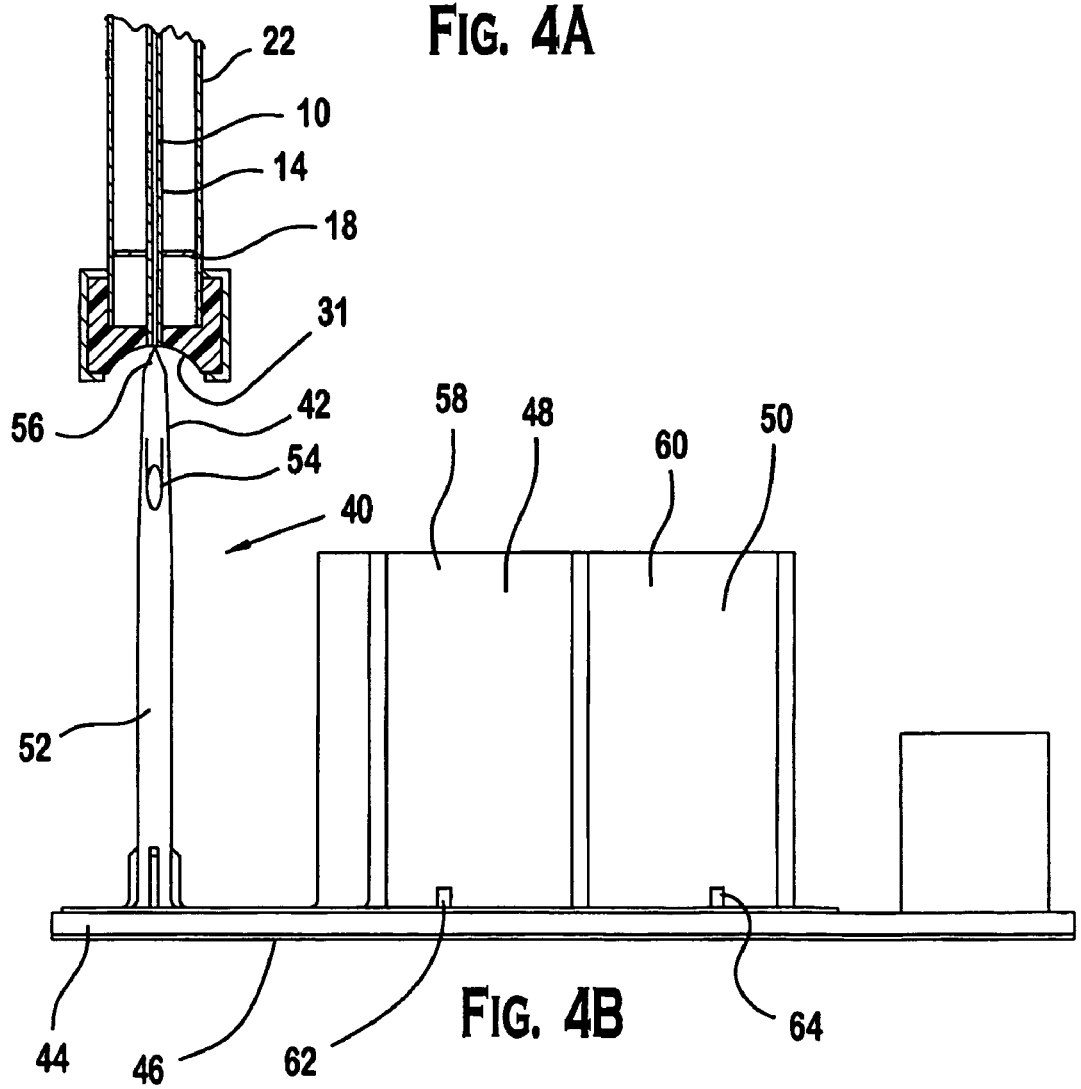
FIG. 4B is a side view of a filtration cell used in conjunction with the clot retainer of the present invention.

Referring to FIGS. 4A and 4B, the clot retainer 10 may also be used in conjunction with a microfiltration cell 40 such as that described in U.S. Pat. No. 6,398,956 which is incorporated by reference herein as if fully set forth. The filtration device 40 preferably comprises a spike 42, a flow channel 44, a filter membrane 46, and a first reservoir 48. A second reservoir 50 can be used to process larger specimens 26 or for back and forth flow during processing. The spike 42 has a hollow interior 52 in preferably open, fluid communication with the flow channel 44, and an opening 54 near the tip 56 of the spike 42. The hollow interior 52 is also in fluid communication with the interior space 58, 60 of the first and second reservoirs 48, 50 via the flow channel 44, and is also adapted to be in preferably open, fluid communication with the interior area of a collection tube 22 containing a specimen 26 to be filtered and analyzed.

When used in conjunction with the clot retainer of the present invention 10, the tip 56 of the spike 42 is preferably adapted to pierce the septum 20 of a collection tube 22 containing a specimen 26 that has already been processed with the clot retainer 10 of the present invention (FIG. 3C). The spike 42 presses up against the clot retainer 10 causing the clot retainer 10 to be fully inserted into the collection tube 22. The end of the clot retainer shaft 14 that contacts the tip 56 of the spike 42 preferably includes a recess (not shown) for receiving the tip 56 of the spike 42. The opening 54 near the tip 56 of the spike 42 is then positioned to be in fluid communication with the serum 34 portion of the specimen 26 in the collection tube 22. The serum 34 flows down the hollow interior 52 of the spike 42 into the flow channel 44 and then to the interior portions 58, 60 of the first and second reservoirs 48, 50 via reservoir openings 62, 64. An airtight seal is preferably formed between the collection tube 22 and filtration cell 40 causing the serum 34 to move through the filtration cell 40 due to air pressurization and/or vacuum controls (not shown) acting on the first and second reservoirs 48, 50.

The flow channel 44 which extends between the hollow interior 52 of the spike 42 and the reservoirs 48, 50 is open to the filter membrane 46 so that fluid to be filtered can be directly passed from the collection tube 22 over the filter membrane 46 as it is transferred from the hollow interior 52 of the spike 42, through the flow channel 44 into the reservoirs 48, 50. Once reaching the reservoirs 48, 50, the fluid path can be repeatedly reversed causing the serum 34 to move back and forth (left to right in FIG. 4B) through the flow channel 44 over the filter membrane 46, where the filtrate is then collected.

Referring to FIGS. 1-4B, one method of harvesting serum 34 from a patient blood specimen 26, operates as follows. A container enclosing a patient blood specimen is provided. The container 22 has a closure 20 and a base 23 and is preferably a test tube.

The clot retainer 10 is provided that includes the elongate shaft 14 with the piercing tip 12 positioned thereon and the fingers 16, 18 mounted on the shaft 14. The fingers 16, 18 can be organized in a single set or grouping or in multiple sets without departing from the present invention. It is preferred that clot retainer have the first set of fingers 16 positioned on the shaft 14 and the second set of fingers 18 positioned on the shaft 18 and axially spaced apart from the first set of fingers 16.

The clot retainer 10 is inserted, piercing tip 12 first, into the container 22 by piercing the closure 20 with the piercing tip 12. Solid components 24 are displaced from the patient blood specimen 26 by the fingers 16, 18 toward the base 23 of the container 22.

In one embodiment of the method of the present invention, the clot retainer 10 is inserted through the closure 20 until the second end 29, opposite from the end on which piercing tip 12 is positioned, of the shaft 14 is generally aligned with the outer surface 31 of the closure 20.

Serum 34 may be removed from the container 22 via the passageway 27 in the elongate shaft. Alternatively, as described above, the shaft 14 can be solid and the serum 34 can be removed from the container 22 via the 42 spike as described below.

When using the spike 42 to withdraw serum 34, the method includes further insertion of the clot retainer 10 into the container 22 such that the entire elongate shaft 14 is located inside the container 22 past the closure 20 by pressing the second end 29 of the elongate shaft 14 toward the base 23 of the container 22 using the spike 42. Then serum 34 can be withdrawn from the patient blood specimen 26 in the container 22 via the spike 42 using gravity or a vacuum. The method of the present invention may also include filtering the serum withdrawn through the spike.

All of the foregoing procedures can be fully automated to further reduce exposure to biohazardous materials and enhance specimen integrity and analytic quality.

Figure 5:
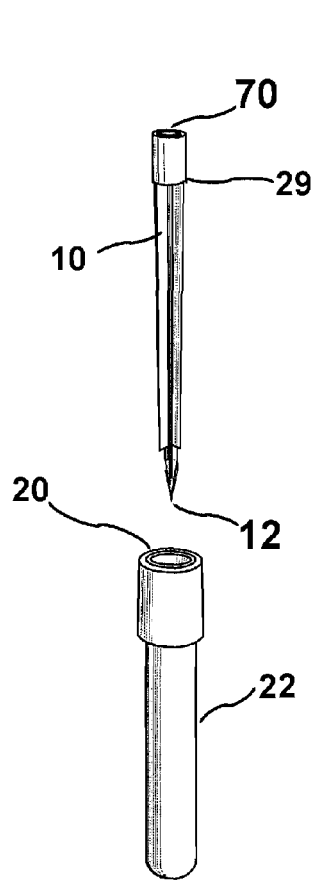
FIG. 5 is a perspective view of the clot retainer of FIG. 1 with a luer lock connector positioned on one end and illustrates the clot retainer aligned with a closure to be pierced by a piercing tip of the clot retainer.

Referring to FIG. 5, the clot retainer 10 may include a luer lock connector 70 on the second end 29. The luer lock container simplifies the connection to other laboratory equipment and simplifies the withdrawal of serum 34 from the container 22.

Figure 6:
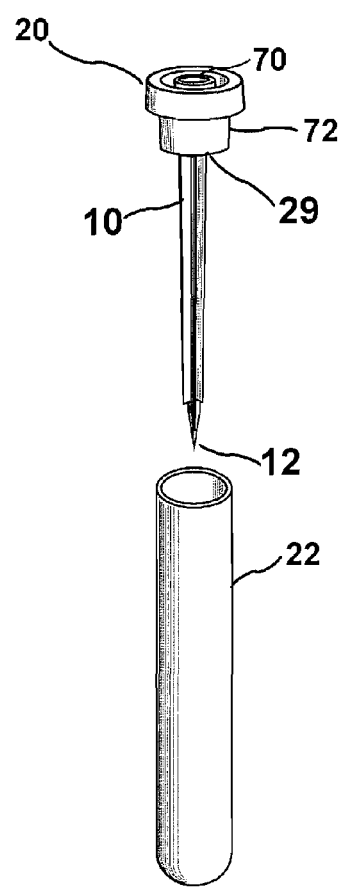

When the container 22 has a relatively small diameter, the associated closure 20 may be too small for convenient piercing. Referring to FIG. 6, when the original enclosure is not conveniently pierced, the clot retainer 10 can be used with a replacement cap 72. The replacement 72 cap can be detachably connected to the clot retainer 10 or can be integrally formed with the clot retainer 10. The cap preferably includes a luer lock connector 70.

Figure 7:
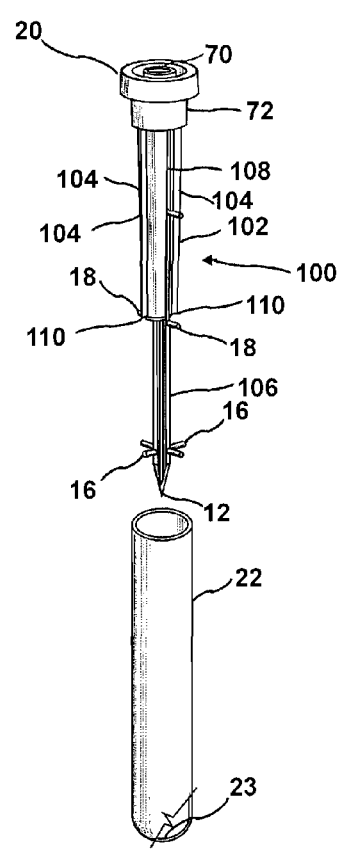
FIG. 7 is a perspective view of the clot retainer according to a second preferred embodiment of the present invention illustrating a two part clot retainer.
Figure 8:
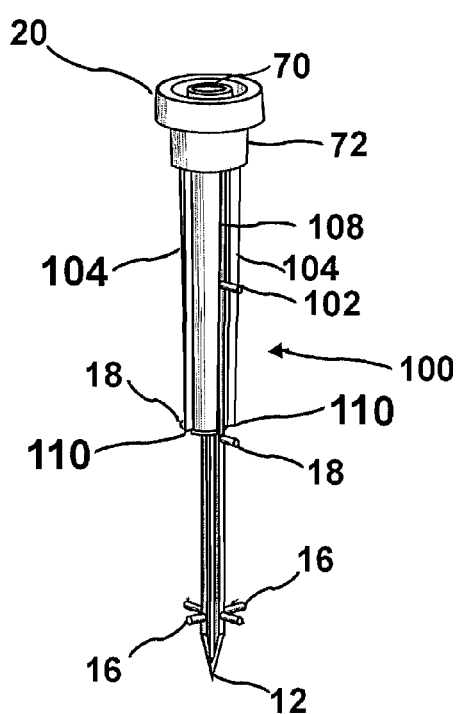
FIG. 8 is an enlarged, perspective view of the clot retainer of FIG. 7 in an extended position.
Figure 9:
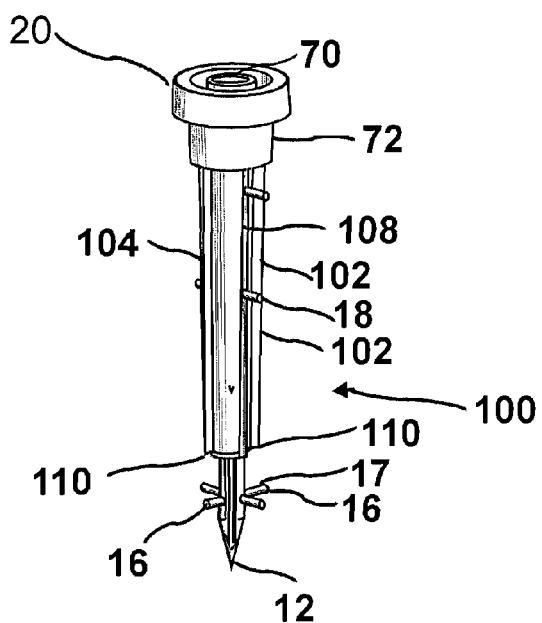
FIG. 9 is a an enlarged, perspective view of the clot retainer of FIG. 7 in a retracted position.

It is preferable, but not necessary, that the piercing tip 12 of the clot retainer 10 abut the bottom of the container 22 to provide maximum separation of serum 34 from the sample. Sometimes, containers 22 have an irregular or non typical length. Referring to FIGS. 7-9, the second embodiment of the clot retainer 100 has an adjustable length to accommodate containers 22 of various lengths. The clot retainer 100 includes a base member 102 that is connected to a replacement cap 72 that preferably has a luer lock connector 70 thereon. The base member 102 preferably includes multiple fins 104 that may be coplanar. A piercing member 106 is slidably engaged with the base member and has fins 16, 18 extending therefrom that operate in a similar fashion to that described above in connection with the first embodiment of the clot retainer 10.

The second preferred clot retainer 100 is preferably received by a user in the extended position. The tolerance of the fit between the base and piercing members 102, 106 is preferably such that there is some resistance to sliding of the piercing member 106. The amount of resistance is preferably enough for the piercing tip 12 to pierce most clots. When the resistance between the base member 102 and the piercing member 1065 is not sufficient to dislodge a clot, it is preferred that the lower, outer corners 110 of the fins 104 provide the necessary force to dislodge the clot.

Once the piercing tip reaches the base 23 of the container 22, further pressure on the base member 102 or the replacement closure 72 results in the piercing member 106 moving further onto and/or into the base member 102 until the replacement closure is secured on the container 22. One advantage of the clot retainer 100 having the same length as the inside of the container 22 is that the fingers 16, 18 provide the maximum separation between any clot and the serum 34. Also, by securing any clot securely against the base 23 of the container 22, fewer clot particles are likely to be dislodged during movement of the container 22. The clot retainer 100 is shown in the retracted position in FIG. 9. Passageways 108 preferably extend through the base member 102 and the piercing member 106 to allow serum 34 to flow through the luer connector 70 or any suitable known connector/passageway.

Figure 10:
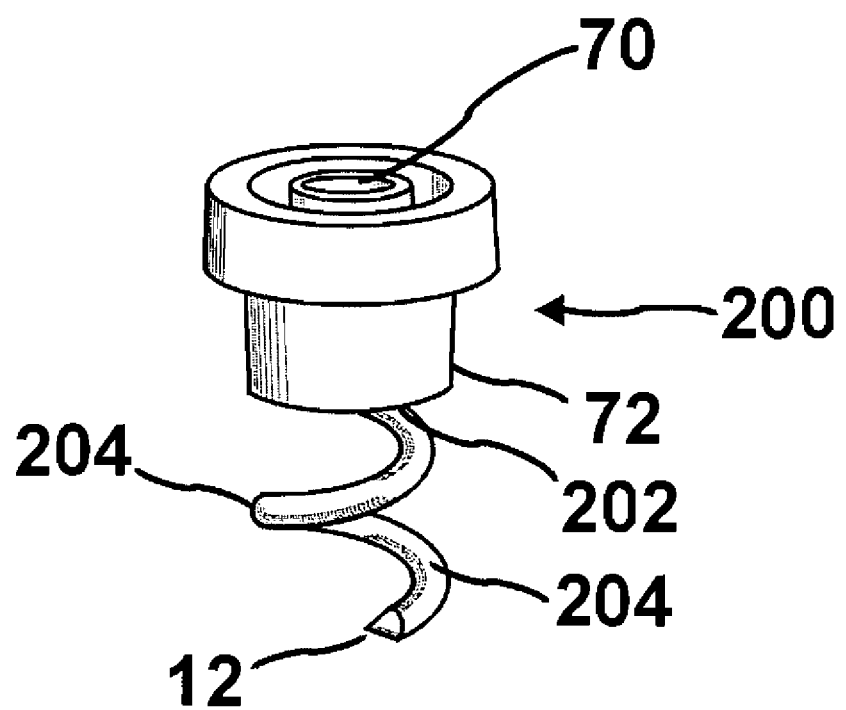
FIG. 10 is a perspective view of a clot retainer according to a third preferred embodiment of the present invention.

Referring to FIG. 10, a third preferred embodiment of the clot retainer 200 includes a replacement closure 72 with a depending coil 202. The coil 202 preferably includes a piercing tip 12 at a lower end. The replacement closure may include a luer lock connection 70. Coil windings 204 provide the clot retaining function served by the fingers 16, 18 in the first and second embodiments. The number of coil windings 204 can be varied depending on the length of the tube and the particular application without departing from the present invention.

This description is based on applications in medical diagnostics using whole blood as the specimen and serum as the test sample. This invention should not, however, be limited exclusively to these specimens or samples, and can include any liquid or gelatinous sample as used in pharmaceutical, biotechnology or other industrial laboratories (i.e. cell culture or fermentation samples) or industrial or chemical processes involving aggregate formation and solid/semi-solid liquid separation.

While various methods, configurations, and features of the present invention have been described above and shown in the drawings for the various embodiments of the present invention, those of ordinary skill in the art will appreciate from this disclosure that any combination of the above features can be used without departing from the scope of the present invention. Accordingly, it is recognized by those skilled in the art that changes may be made to the above described methods and embodiments of the invention without departing from the broad inventive concept thereof. It is understood, therefore, that this invention is not limited to the particular methods and embodiments disclosed, but is intended to cover all modifications which are within the spirit and scope of the invention as defined by the appended claims and/or shown in the attached drawings.

What is claimed is:

1. A clot retainer for generally separating serum from a patient blood specimen enclosed in a container having a closure, the clot retainer comprising:
   an elongate shaft;
   a piercing tip positioned on an end of the elongate shaft to pierce the closure on the container to insert the clot retainer into the container without removal of the closure; and
   fingers to displace solid components of the patient blood specimen toward a base of the container while allowing the serum to flow through interstices between the fingers, each of the fingers comprising a solid extension member having a first end connected to the elongate shaft and a second free end and being moveable from a first position, in which the finger is ready for use and is in a generally radially extending position, to a second position, in which the finger is ready for insertion and is in a generally axially extending position along the elongate shaft, each of the fingers being in the second position during insertion prior to returning to the first position after insertion.

2. The clot retainer of claim 1, wherein the elongate shaft includes at least one recess to receive at least one of the fingers therein during insertion of the clot retainer through the closure.

3. The clot retainer of claim 1, wherein the piercing tip is generally conically shaped and has a base, located proximate to the elongate shaft, having a base diameter greater than a shaft diameter of the elongate shaft.

4. The clot retainer of claim 3, wherein a general overall diameter of the elongate shaft and the fingers, when the fingers are in the second position, is generally the same as or less than the base diameter of the piercing tip.

5. The clot retainer of claim 1, wherein the fingers comprise a first set of the fingers that extend radially outwardly from a first portion of the shaft in the first position.

6. The clot retainer of claim 5, wherein the fingers further comprise a second set of the fingers positioned on the elongate shaft and axially spaced from the first set of the fingers.

7. The clot retainer of claim 5, wherein a width, as measured in a direction tangential to a cross section of the elongate shaft as taken perpendicular to a longitudinal axis thereof, of each of the fingers is generally constant.

8. The clot retainer of claim 5, wherein at least one of the plurality of fingers is generally rectilinearly shaped.

9. The clot retainer of claim 5, wherein a width, as measured in a circumferential direction, of each of the fingers increases when moving along the fingers in a generally radially outward direction.

10. The clot retainer of claim 5, wherein at least one of the fingers is generally wedge-shaped.

11. The clot retainer of claim 5, wherein the first set of the fingers generally forms a layer having a permeable free space of generally less than fifty (50%) percent.

12. The clot retainer of claim 11, wherein the layer has a permeable free space of generally less than twenty-five (25%) percent.

13. The clot retainer of claim 11, wherein the fingers further comprise a second set of the fingers positioned on the elongate shaft and spaced apart from the first set of the fingers.

14. The clot retainer of claim 1, further comprising a passageway through at least a portion of the elongate shaft to allow withdrawal of serum from the container while the elongate shaft is positioned through the closure.

15. The clot retainer of claim 1, wherein the fingers are formed of an elastic material and move elastically from the second position to the first position.

16. The clot retainer of claim 1, wherein the elongate shaft comprises:
   a base member; and
   a piercing member slidably disposed on the base member, the piercing tip being positioned on an end of the piercing member distal from the base member.

17. The clot retainer of claim 1, wherein the fingers are connected to the elongate shaft at a position apart from the piercing tip.

18. The clot retainer of claim 1, wherein the entire length of the fingers are foldable along the elongate shaft in the axially extending position.

19. A clot retainer for generally separating liquid from solid in a specimen enclosed in a container having a closure, the clot retainer comprising:
   an elongate shaft;
   a piercing tip positioned on an end of the elongate shaft to pierce the closure on the container to insert the clot retainer into the container without removal of the closure; and
   specimen separation fingers to displace solid components of the specimen toward a base of the container while allowing the liquid to flow through interstices between the specimen separation fingers, each of the specimen separation fingers comprising a solid extension member having a first end and a second free end, the first end of the specimen separation fingers connected to the elongate shaft at a position apart from the piercing tip and being moveable from a first position, in which the specimen separation finger is ready for use and is in a generally radially extending position, to a second position, in which the specimen separation finger is ready for insertion and is in a generally axially extending position along the elongate shaft, each of the specimen separation fingers being in the second position during insertion prior to returning to the first position after insertion.

20. A method of harvesting serum from a patient blood specimen, the method comprising the steps of:
   providing a container enclosing a patient blood specimen, the container having a closure and a base;
   providing a clot retainer comprising an elongate shaft having a piercing tip positioned thereon and solid elongated fingers extending from the elongate shaft;
   inserting the clot retainer, piercing tip first, into the container by piercing the closure with the piercing tip, the solid elongated fingers displacing solid components of the patient blood specimen toward the base of the container to separate the solid components from serum components in the patient blood specimen; and harvesting the separated serum components from the container.

21. The method of claim 20, wherein the step of providing the container comprises providing a test tube.

22. The method of claim 21, wherein the step of providing the clot retainer further comprises providing the clot retainer having a first set of the fingers positioned on the elongate shaft and a second set of the fingers positioned on the elongate shaft and axially spaced apart from the first set of the fingers.

23. The method of claim 20, wherein the step of inserting the clot retainer comprises inserting the clot retainer until a second end, opposite from an end on which the piercing tip is positioned, of the elongate shaft is generally aligned with an outer surface of the closure.

24. The method of claim 23, further comprising the step of further inserting the clot retainer into the container such that the entire elongate shaft is located inside the container past the closure by pressing the second end of the elongate shaft toward the base of the container using a spike.

25. The method of claim 24, further comprising withdrawing serum from the patient blood specimen in the container via the spike.

26. The method of claim 25, wherein the step of withdrawing serum comprises gravity pulling the serum from the container through the spike.

27. The method of claim 25, further comprising filtering the serum withdrawn through the spike.

28. The method of claim 20, further comprising the step of removing serum from the container via a passageway in the elongate shaft.

29. The method of claim 20, further comprising:
folding the fingers into an axially extending position by the fingers contacting the closure during insertion of a portion of the shaft; and
allowing the fingers to unfold elastically to a radially extending position after passing through the closure.

30. The method of claim 20, wherein the step of providing the clot retainer further comprises providing the clot retainer having the elongate shaft, comprising: a base member; and a piercing member slidably disposed on the base member, the piercing tip being positioned on an end of the piercing member distal from the base member.

31. A combination closure and clot retainer for generally separating serum from a patient blood specimen enclosed in a container, the combination comprising:
an elongated shaft, comprising:
a base member having first and second ends; and
a piercing member adjustably disposed on the first end of the base member so as to slidably move onto or into the base member to accommodate containers of various lengths;
a closure positioned on the second end of the base member;
a piercing tip positioned on an end of the piercing member to pierce a clot in the specimen; and
solid elongated fingers connected to the elongate shaft to displace solid components of the patient blood specimen toward a base of the container while allowing the serum to flow through interstices between the fingers.

32. The combination of claim 31, wherein each of the fingers is moveable from a first position, in which the finger is ready for use and is in a generally radially extending position, to a second position, in which the finger is in a generally axially extending position along the elongate shaft, each of the fingers being in the second position during insertion into the container prior to returning to the first position after insertion.

33. The combination of claim 31, wherein each of the fingers are generally rigid and extend in a generally radially extending position.

34. The combination of claim 31, wherein the base member and the piercing member each have a passageway to allow fluid flow through at least a portion of the elongated shaft.

35. The combination of claim 34, wherein the closure includes a luer connection in communication with the passageway.

* * * * *